(12) United States Patent
Peterson et al.

(10) Patent No.: US 11,521,719 B1
(45) Date of Patent: *Dec. 6, 2022

(54) VALENCE PROFILING OF VIRTUAL INTERACTIVE OBJECTS

(71) Applicant: Verily Life Sciences LLC, Mountain View, CA (US)

(72) Inventors: Bret Peterson, Lafayette, CA (US); Collin Walter, San Francisco, CA (US); Merle Fromer, New Rochelle, NY (US); Honor Hsin, Palo Alto, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 259 days.

This patent is subject to a terminal disclaimer.

(21) Appl. No.: 17/026,083

(22) Filed: Sep. 18, 2020

Related U.S. Application Data

(63) Continuation of application No. 15/900,567, filed on Feb. 20, 2018, now Pat. No. 10,818,384.

(51) Int. Cl.
  *G16H 10/60* (2018.01)
  *G16H 50/20* (2018.01)
  *G06F 16/951* (2019.01)

(52) U.S. Cl.
  CPC ........... *G16H 10/60* (2018.01); *G06F 16/951* (2019.01); *G16H 50/20* (2018.01)

(58) Field of Classification Search
  CPC ........ G06Q 50/01; G16H 50/20; G16H 40/67; G16H 50/30; G16H 50/70; G06F 17/40; A61B 5/165
  See application file for complete search history.

(56) References Cited

U.S. PATENT DOCUMENTS

| | | | |
|---|---|---|---|
| 2012/0095976 A1 | 4/2012 | Hebenthal et al. | |
| 2012/0150430 A1 | 6/2012 | French et al. | |
| 2012/0277594 A1 | 11/2012 | Pryor | |
| 2013/0297536 A1 | 11/2013 | Almosni et al. | |
| 2016/0335405 A1* | 11/2016 | Perunov | G06N 20/00 |

* cited by examiner

*Primary Examiner* — Joseph D Burgess
(74) *Attorney, Agent, or Firm* — Perkins Coie LLP

(57) ABSTRACT

Introduced here are health management platforms able to infer the health state of a subject based on behavioral changes reflected in the digital activities performed by a subject. A health management platform can initially acquire contextual data pertaining to digital activities performed by the subject. The health management platform can identify the target(s) of the digital activities by parsing the contextual data, and then compile the digital activities and corresponding activities into a personalized valence index. Thereafter, the health management platform can compare digital activities performed by the subject to the entries included in the personalized valence index. If a matching entry is not discovered, the health management platform can identify an instance of behavior change. These instances of behavior change may be indicative of changes in the subject's health state.

20 Claims, 9 Drawing Sheets

500

501
Acquire contextual data associated with a subject

502
Detect each digital activity represented by the contextual data

503
Identify the target(s) of each digital activity

504
Populate a database entry for each digital activity that associates the digital activity and its corresponding target(s)

505
Compile the database entries into a personalized valence index

506
Update the personalized valence index responsive to detecting new digital activities or new targets

601
Acquire contextual data associated with a subject

602
Detect a digital activity represented by the contextual data

603
Identify the target(s) of the digital activity

604
Access a valence index known to correspond to a certain health state

605
Estimate a health state of the subject by comparing the digital activity or the target(s) to entries included in the valence index

Receive input specifying whether digital activities, targets, or any combination thereof are indicative of positive or negative valence

702

Populate a database entry for each digital activity

703

Compile the database entries into a population-level valence index

704

Associate the population-level valence index with a certain health state

FIGURE 7

VALENCE PROFILING OF VIRTUAL INTERACTIVE OBJECTS

CROSS-REFERENCE TO RELATED APPLICATION

This application is a continuation of U.S. patent application Ser. No. 15/900,567, titled "VALENCE PROFILING OF VIRTUAL INTERACTIVE OBJECTS" and filed on Feb. 20, 2018, which is incorporated by reference herein in its entirety.

TECHNICAL FIELD

Various embodiments concern computer programs and associated computer-implemented techniques for assessing the health state of a subject based on the objects involved in activities involving the subject.

BACKGROUND

Contemporary research has begun exploring how media content affects the emotional health state. Such research has considered emotion as a predictor of media selection, an outcome of media exposure, a mediator of other psychological/behavioral outcomes resulting from media exposure, etc.

For example, several studies have examined the emotional consequences of using social media (e.g., Facebook® or Twitter®). These studies have shown that the use of social media can cause both positive feelings and negative feelings, which can facilitate or hinder the development of social capital and social connectedness. However, these studies often fail to account for how the emotional health state impacts which media content is consumed by an individual.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

FIG. 5 depicts a flow diagram of a process for generating a personalized valence index for a subject.

FIG. 6 depicts a flow diagram of a process for discovering changes in the health state of a subject through the application of a valence index.

FIG. 7 depicts a flow diagram of a process for generating a population-level valence index.

Figure 1:
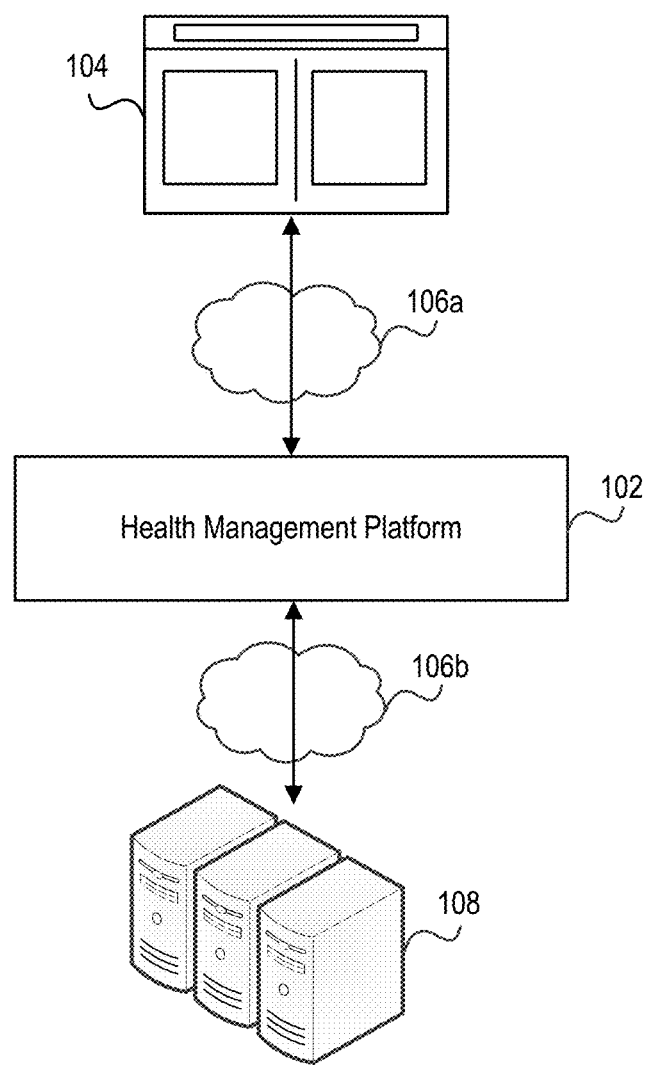
FIG. 1 illustrates a network environment that includes a health management platform.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Clinical interactions with individuals (also referred to as "patients" or "subjects") are often infrequent, so it can be difficult for a clinician to follow transitions in the health state of a subject at an optimal temporal resolution. This is particularly true for at-risk subjects and subjects that have recently been prescribed new medications, treatments, etc.

Entities have begun developing healthcare-focused computer programs that can automatically identify, monitor, and promote different aspects of physical, mental, and emotional well-being. Some computer programs expressly solicit feedback directly from subjects (e.g., via manually populated forms), while other computer programs continually track subject behaviors along multiple dimensions without requiring user input. For example, a computer program may monitor user interactions with a social media application that resides on a mobile phone. As another example, a computer program may monitor user interactions with a calling application or a messaging application that resides on a mobile phone.

Classification algorithms can then be applied by the computer program to detect deviations from routine patterns. By applying the classification algorithms, the computer program can automatically assess the health state based on health characteristics inferred from these subject behaviors. Health characteristics can include, for example, estimated sleep duration, physical activities, communication activities, and social interactions.

However, these computer programs cannot capture much of the contextual resolution necessary to fully understand the health implications of various activities. For example, conventional technologies simply consider whether these activities occurred, rather than the nature of the objects involved in these activities. Said another way, conventional technologies are often unable to accurately estimate the health state in a non-invasive manner because limited information is considered. Having an accurate understanding of most, if not all, activities affecting the health state can be critical in providing diagnoses, monitoring disease or risk progression, suggesting treatment options, etc.

Introduced here, therefore, are health management platforms able to monitor changes in the health state of a subject based on the context of digital activities performed by, or involving, the subject. More specifically, the health management platforms can examine contextual data associated with digital activities to determine whether the objects involved in the digital activities are indicative of positive or negative valence. The term "digital activity" can refer to actions completed using an electronic medium (e.g., calling, messaging, or browsing activities) and actions capable of being virtually represented (e.g., movement activities from location data, physical activities from activity data, or medication activities from healthcare data).

The term "health state," meanwhile, can refer to physical health, mental health, emotional health, or any combination thereof. For example, some health management platforms are designed to identify/monitor digital activities known to be indicative of a episodic psychiatric disorder (e.g., depression or schizophrenia), while other health management platforms are designed to identify/monitor digital activities known to be indicative of chronic physical ailments (e.g., diabetes or Chron's disease).

A health management platform can monitor the occurrence/performance of digital activities in real time, and then virtually represent each digital activity based on corresponding contextual data. Generally, a virtual representation of a digital activity will specify the nature of the digital activity itself, as well as the object(s) of interest involved in the digital activity.

For example, each time a subject uses a map application to facilitate a movement activity, the map application can generate contextual data that includes a record of movement activities involving the subject. In such instances, each movement activity represents a digital activity, and the object of interest (also referred to as the "target") of the digital activity is a geographical location, such as the origination point and/or the destination point. The geographical location may be specified using a Global Positioning System (GPS) coordinate, a wireless access point (WAP) identifier, or any combination thereof.

As another example, each time a subject uses a social media application to facilitate a social activity, the social media application can generate contextual data that includes a record of social activities involving the subject. In such instances, each social activity represents a digital activity, and the target of the digital activity may be a social media identifier involved in the social activity. Examples of social media identifiers include account identifiers (e.g., usernames and handles), communication identifiers (e.g., phone numbers, groups, and email addresses), etc. In some embodiments contextual data related to social activities is received from a social media platform responsible for supporting the social media application (e.g., from a cloud-based platform via an application programming interface), while in other embodiments contextual data related to social activities is received directly from the social media application.

As another example, each time a subject uses a web browser application to facilitate an internet activity, the web browser application can generate contextual data that includes a record of internet activities involving the subject. In such instances, each internet activity represents a digital activity, and the target of the digital activity may be the term(s) submitted in a search query, the visited website, etc.

A health management platform can acquire contextual data associated with digital activities involving a subject from one or more different sources. For example, the health management platform may simultaneously or sequentially acquire contextual data from the map application, the social media application, and the web browser application, as well as the computing device on which these applications reside.

The health management platform can then compile the contextual data into a personalized valence index that digitally characterizes the health state of the subject. Said another way, digital activities included in the contextual data may indicate health state if the subject initiates the digital activities or health influences if the digital activities are controlled (e.g., a call placed by the subject to a first person may indicate the subject is in a good mood, while a call received by the subject from a second person may increase the likelihood the subject is, or will soon be, in a worse mood). More specifically, the health management platform can configure the personalized valence index based on the targets of the digital activities represented by the contextual data. Thus, the personalized valence index can provide a model of digital activities typically performed by the subject.

Thereafter, the health management platform can acquire new contextual data associated with a recently completed digital activity involving the subject. The health management platform can analyze the new contextual data to identify a target of the digital activity, and then calculate a valence measure based on the digital activity and/or the target. This can occur in several different ways.

In some embodiments, the health management platform estimates the valence measure by determining whether the digital activity and/or the target matches any entries included in the personalized valence index. Generally, the health management platform will determine that a "match" was found if a substantially similar digital activity or a substantially similar target is discovered.

In other embodiments, the health management platform estimates the valence measure by calculating the natural valence of the digital activity and/or the target. The natural valence may be based on the nature of the digital activity or the target. For example, if the digital activity is the submittal of a search query, then the natural valence may be based on the valence of the term(s) submitted in the search query.

Valence measures produced by the health management platform can facilitate the discovery of potential triggers/causes of a symptomatic onset, instances for intervention, trends in the health state, etc. The individual may be the subject whose health state is being monitored or a health coach responsible for monitoring the health state of the subject.

The health management platform may also train the personalized valence index over time upon receiving new contextual data. In some instances, the new contextual data may reaffirm the personalized valence index (e.g., by including similar digital activities and/or similar targets). In other instances, the new contextual data may prompt an update to the personalized valence index (e.g., by including different digital activities and/or different targets).

Because the targets of digital activities can be derived from contextual data, the health management platform can determine the heath state in a non-invasive manner (e.g., without directly inquiring about a digital activity or notifying the subject that such analysis is occurring). This may be particularly useful in scenarios where subjects are less willing to expressly divulge details that are critical in determining the health state (e.g., when the health management platform is designed to monitor mental or emotional health). This may also be useful in scenarios where subjects are less likely to remember certain details or lie regarding the certain details (e.g., if a subject were prompted to specify all websites visited or search queries submitted via a web browser application).

Embodiments may be described with reference to particular computer programs, system configurations, networks, etc. However, those skilled in the art will recognize that these features are equally applicable to other computer program types, system configurations, network types, etc. For example, although the term "application" may be used to describe a computer program, the relevant feature may be embodied in another type of computer program.

Moreover, the technology can be embodied using special-purpose hardware (e.g., circuitry), programmable circuitry appropriately programmed with software and/or firmware, or a combination of special-purpose hardware and programmable circuitry. Accordingly, embodiments may include a machine-readable medium having instructions that may be used to program a computing device to perform a process for examining contextual data pertaining to digital activities involving a subject, identifying the targets of the digital activities, generating a personalized valence index for the subject based on the digital activities and/or targets, applying the personalized valence index to determine a health state, etc.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of steps performed in any of the processes described here are exemplary. However, unless contrary to physical possibility, the steps may be performed in various sequences and combinations. For example, steps could be added to, or removed from, the processes described here. Similarly, steps could be replaced or reordered. Thus, descriptions of any processes are intended to be open-ended.

Technology Overview

FIG. 1 illustrates a network environment 100 that includes a health management platform 102. Individuals can interface with the health management platform 102 via an interface 104. The health management platform 102 may be responsible for parsing contextual data to detect occurrences of digital activities, identify the target(s) of each digital activity, estimate a health state based on the digital activities and/or targets, etc. The health management platform 102 may also be responsible for creating interfaces through which the individual can view media content (e.g., journal entries, feedback forms, and recommendations for improving the health state), review estimations of the health state, manage preferences, etc.

Contextual data could pertain to digital activities involving the individual accessing the interface 104 or some other person. For example, in some embodiments the interface 104 enables a person whose health state is being monitored to view their own contextual data (or analysis of such data), while in other embodiments the interface an individual to view contextual data (or analysis of such data) associated with some other person. The individual may be a health coach responsible for monitoring the health state of the other person. Examples of health coaches include medical professionals (e.g., a physician, nurse, or psychiatrist), mental health counselors, family members of the other person, etc. Some interfaces are configured to facilitate interactions between subjects and health coaches, while other interfaces are configured to serve as informative dashboards for subjects.

As noted above, the health management platform 102 may reside in a network environment 100. Thus, the health management platform 102 may be connected to one or more networks 106a-b. The network(s) 106a-b can include personal area networks (PANs), local area networks (LANs), wide area networks (WANs), metropolitan area networks (MANs), cellular networks, the Internet, etc. Additionally or alternatively, the health management platform 102 can be communicatively coupled to computing device(s) over a short-range communication protocol, such as Bluetooth® or Near Field Communication (NFC).

The interface 104 is preferably accessible via a web browser, desktop application, mobile application, or over-the-top (OTT) application. Accordingly, the interface 104 may be viewed on a personal computer, tablet computer, personal digital assistant (PDA), mobile phone, game console, music player, wearable electronic device (e.g., a watch or fitness accessory), network-connected ("smart") electronic device, (e.g., a television or home assistant device), virtual/augmented reality system (e.g., a head-mounted display), or some other electronic device.

Some embodiments of the health management platform 102 are hosted locally. That is, the health management platform 102 may reside on the computing device used to access the interface 104. For example, the health management platform 102 may be embodied as a mobile application executing on a mobile phone. Other embodiments of the health management platform 102 are executed by a cloud computing service operated by Amazon Web Services® (AWS), Google Cloud Platform™, Microsoft Azure®, or a similar technology. In such embodiments, the health management platform 102 may reside on a host computer server that is communicatively coupled to one or more content computer servers 108. The content computer server(s) 108 can include media content (e.g., journal entries produced by subjects and forms populated by subjects), user information (e.g., profiles, credentials, and health-related information such as age, mental health diagnoses, etc.), and other assets. Such information could also be stored on the host computer server.

Certain embodiments are described in the context of network-accessible interfaces. However, those skilled in the art will recognize that the interfaces need not necessarily be accessible via a network. For example, a computing device may be configured to execute a self-contained computer program that does not require network access. Instead, the self-contained computer program may cause necessary assets (e.g., contextual data, personalized valence index, healthcare regimen data, or processing operations) to be downloaded at a single point in time or on a periodic basis (e.g., weekly, daily, or hourly).

Figure 2:
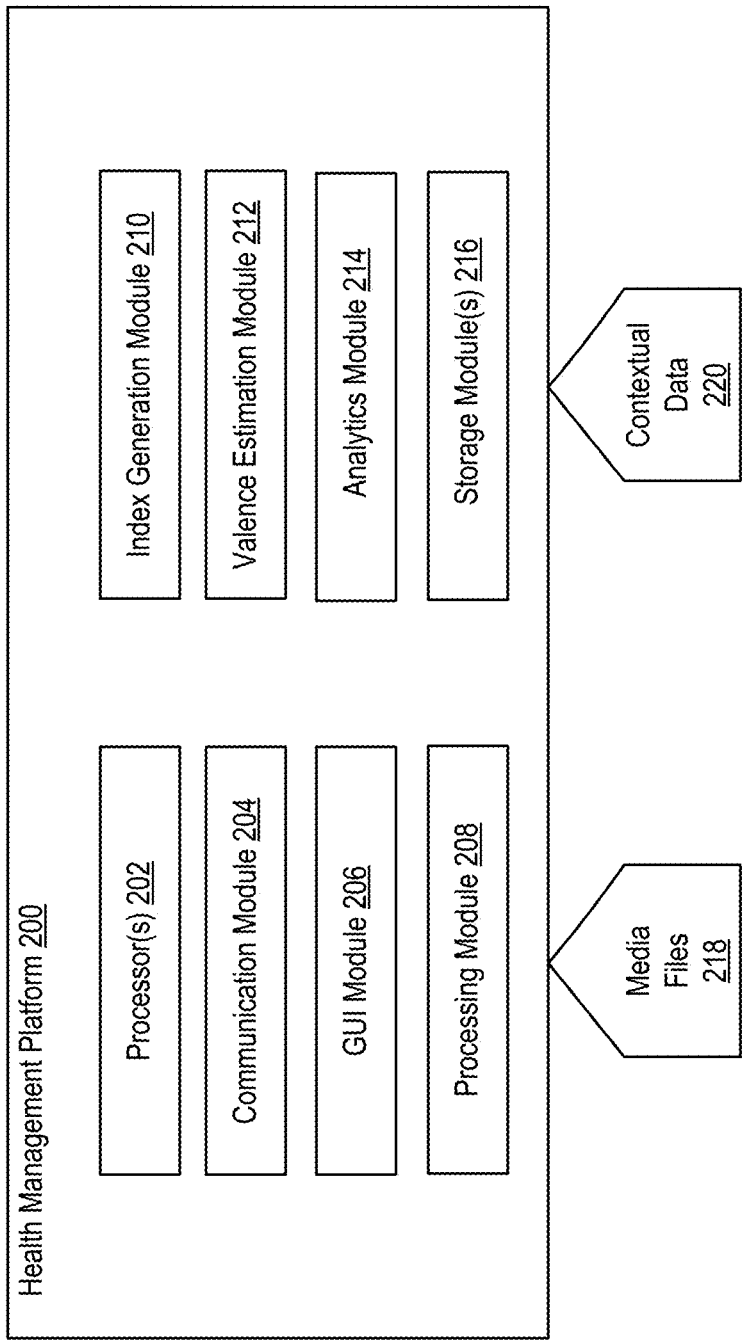
FIG. 2 depicts the high-level architecture of a health management platform able to generate a personalized valence index for a subject based on contextual data acquired from one or more sources.

FIG. 2 depicts the high-level architecture of a health management platform 200 able to generate a personalized valence index for a subject based on contextual data acquired from one or more sources. The health management platform 200 may use the personalized valence index to monitor the health state of the subject over time. As shown in FIG. 1, an individual can interface with the health management platform 200 via an interface. The individual may be a subject whose health state is being monitored or another person with an interest in the health state of the subject.

The health management platform 200 can include one or more processors 202, a communication module 204, a graphical user interface (GUI) module 206, a processing module 208, an index generation module 210, a valence estimation module 212, an analytics module 214, and one or more storage modules 216. In some embodiments a single storage module includes multiple computer programs for performing different operations (e.g., metadata extraction, format conversion, and feature analysis), while in other embodiments each computer program is hosted within a separate storage module. Embodiments of the health management platform 200 may include some or all of these components, as well as other components not shown here.

The processor(s) 202 can execute modules from instructions stored in the storage module(s) 216, which can be any device or mechanism capable of storing information. For example, the processor(s) 202 may execute the GUI module 206, processing module 208, index generation module 210, valence estimation module 212, and analytics module 214.

The communication module 204 can manage communications between various components of the health management platform 200. The communication module 204 can also manage communications between the computing device on which the health management platform 200 resides and another computing device.

For example, the health management platform 200 may reside on a mobile phone in the form of a mobile application. In such embodiments, the communication module 204 can facilitate communication with a network-accessible computer server responsible for supporting the mobile application. The communication module 204 may facilitate communication with various data sources through the use of application programming interfaces (APIs), bulk data interfaces, etc. Examples of data sources include network-accessible databases, other mobile applications residing on the mobile phone, etc.

As another example, the health management platform 200 may reside on a server system that includes one or more network-accessible computer servers. In such embodiments, the communication module 204 can communicate with a computer program executing on the computing device associated with the individual. Those skilled in the art will recognize that the components of the health management platform 200 can be distributed between the server system and the computing device associated with the individual in various manners. For example, some data (e.g., contextual data) may reside on the computing device of the individual, while other data (e.g., processing operations for detecting digital activities in contextual data, generating a personalized valence index, and estimating the health state) may reside on the server system.

The GUI module 206 can generate the interface(s) through which an individual can interact with the health management platform 200. For example, an interface may include a graphical representation of the current health state or the health state over a certain period of time. As another example, an interface may include media content corresponding to the current health state. For instance, uplifting media content may be shown in response to determining that the individual has performed digital event(s) having negative valence (e.g., causing a downward shift in mood or emotion), while supportive media content may be shown in response to determining that the individual has performed digital event(s) having positive valence (e.g., causing an upward shift in mood or emotion).

These interfaces may also present feedback/suggestions for improving the health state. For example, if the health management platform 200 determines that the individual has performed a digital activity having negative valence, then the health management platform 200 may recommend that the individual perform a digital activity known to have positive valence. That is, the health management platform 200 may recommend the individual perform digital activities likely to improve the health state. As further described below, these recommendations can be personalized by the health management platform 200, which may know which digital activities have positive valence when performed by the individual through the generation of a personalized valence index.

The processing module 208 can apply one or more operations to contextual data 220 acquired by the health management platform 200. As further described below, the contextual data 220 could be acquired from one or more sources. Examples of sources include the computing device on which the health management platform 200 resides, a computer program executing on the computing device, and some other computing device. Contextual data 220 will often be acquired by the health management platform 200 from multiple sources. Thus, the processing module 208 may apply operation(s) to the contextual data 220 to ensure that contextual data 220 received from multiple sources is in a compatible format.

The processing module 208 can also apply one or more operations to media files 218 acquired by the health management platform 200. Each media file could correspond, for example, to a different journal entry produced by a subject or a different form manually populated by the subject. Media files 218 could include text media, audio media, video media, or any combination thereof. For example, some media files may only include text media, while other media files may include only audio media. In some embodiments the contextual data 220 accompanies the media files 218, while in other embodiments the contextual data 220 is extracted or derived from the media files 218.

A source may be configured to continuously or periodically transmit media files 218 and/or contextual data 220 to the health management platform 200. In some embodiments, the source continually uploads media files 218 and/or contextual data 220 to the health management platform 200 so long as the source remains communicatively coupled to the computing device on which the health management platform 200 resides (e.g., via a Bluetooth® communication channel). In other embodiments, the source uploads media files 218 and/or contextual data 220 to the health management platform 200 on a periodic basis (e.g., hourly, daily, or weekly). The health management platform 200 can be configured to pull media files 218 and/or contextual data 220 from the source. Additionally or alternatively, the source can be configured to push media files 218 and/or contextual data 220 to the health management platform 200. In some embodiments, the subject or an administrator (e.g., a health coach or an individual responsible for supporting the health management platform 200) is able to configure these push/pull settings. These settings can be configured on an individual basis or group basis (e.g., for multiple subjects that share a health characteristic in common).

The processing module 208 can process the contextual data 220 into a format suitable for the other modules (e.g., the index generation module 210, valence estimation module 212, analytics module 214, or storage module(s) 216). The processing module 208 can also parse the contextual data 220 to identify the subject and/or occurrences of digital activities. The term "digital activity" can refer to actions completed using an electronic medium and actions capable of being virtually represented. Examples of digital activities include communication activities (e.g., completing a call, text, or email), browsing activities (e.g., visiting a website or submitting a search query), movement activities (e.g., traveling in accordance with directions provided by a map application), physical activities (e.g., waking a computing device), social activities (e.g., initiating an interaction via social media), etc. For example, the processing module 208 may identify the subject by parsing the contextual data 220 to discover a feature indicative of the subject (e.g., an identifier or characteristic conveyed by metadata). Additionally or alternatively, the processing module 208 may discover the contextual data 220 is associated with the subject based on the source responsible for providing the contextual data 220 (e.g., a computer program that provides the contextual data 220 may know the subject is currently signed in).

The index generation module 210 can examine the contextual data 220 to identify digital activities involving the subject. More specifically, the index generation module 210 can detect the digital activities by parsing the contextual data 220, and then represent each digital activity as a virtual object. Generally, a virtual object corresponding to a digital activity will specify the nature of the digital activity itself, as well as the target(s) of the digital activity. Examples of targets include:

- A destination point;
- An origination point;
- A type of location visited (e.g., a school, amusement park, or home belonging to a family member);
- A likelihood of human interaction (e.g., based on location and/or time);
- A duration spent outdoors/indoors;
- A duration spent performing a recreational activity;
- An indication as to the amount of weather/light exposure;
- An indication as to the amount of traffic or the amount of time spent commuting;
- Term(s) submitted within a search query;
- A website visited during a browsing session;
- An identity of a person (e.g., the recipient of a call, text, or email message);
- An identification of a person's class (e.g., family member, friend, coworker, health coach, etc.);
- An indication as to the frequency of interactions with a person;
- A count of scheduled events;
- A count of skipped scheduled events;
- A count of rescheduled events;
- A time spent consuming media content;
- A media file (e.g., an audio or video file);
- A comment associated with the media file;
- A measure of correlation with others consuming the media file;
- A frequency of self-reported feedback (e.g., journal entries, notes, and forms);
- Content of the self-reported feedback;
- An image taken by a computing device; and
- A frequency of images taken by the computing device.

Moreover, the index generation module 210 may consider valence measures associated with some or all of these targets.

The index generation module 210 can compile these virtual objects into a personalized valence index that digitally characterizes the health state of the subject. As noted above, the term "health state" can refer to physical health, mental health, emotional health, or any combination thereof. Thus, the personalized valence index can provide a model of digital activities typically performed by the subject.

Thereafter, the health management platform 200 may acquire new contextual data associated with a recently completed digital activity involving the subject. In such scenarios, the valence estimation module 212 can analyze the new contextual data to identify a target of the digital activity, and then calculate a valence measure based on the digital activity and/or the target. This can occur in several different ways.

In some embodiments, the valence estimation module 212 estimates the valence measure by determining whether the digital activity and/or the target matches any entries included in the personalized valence index. Generally, the valence estimation module 212 will determine that a "match" was found if a substantially similar digital activity or substantially similar target is discovered. Some embodiments of the valence estimation module 212 are configured to identify a matching entry only if a substantially similar digital activity and target are discovered. For example, if the digital activity is a phone call to a family member, then a matching record may need to include another phone call to the same family member. As another example, if the digital activity is a search query, then a matching record may need to include another search query including the same or similar term(s).

In other embodiments, the valence estimation module 212 estimates the valence measure by calculating the natural valence of the digital activity and/or the target. The natural valence may be based on the nature of the digital activity or the target. Such analysis can examine a paralinguistic feature, a non-linguistic feature, a linguistic feature, or any combination thereof.

Paralinguistic features refer to those aspects of communication that do not involve speech. Paralinguistic features often add emphasis or shades of meaning to what an individual says. Examples of paralinguistic features include body language, gestures, facial expressions, etc. Non-linguistic features refer to those aspects of spoken communication that do not involve words. Much like paralinguistic features, non-linguistic features can add emphasis or shades of meaning to what an individual says. Examples of non-linguistic features include tone, pitch, volume/loudness, speaking rate, shimmer, jitter, etc. Linguistic features, meanwhile, refer to those aspects of spoken communication that do involve words. Examples of linguistic features include the word count of different n-grams, whether jargon/slang is used, etc.

Accordingly, if the digital activity is the submittal of a search query, then the natural valence may be based on feature(s) identified from an examination of the search query. Examples of speech features include:

Word Count—Word count specifies the total number of words included in the search query.

Word Count of N-grams—Prior studies have found connections between the language used in social media (e.g., on Facebook® or Twitter®) and health state. Thus, the valence estimation module 212 may detect the total number of words in certain n-gram categories that correlate with health state. Moreover, the valence estimation module 212 may detect strings of multiple words corresponding to certain n-gram categories that are stronger indicators of health state (e.g., "severe" and "addiction" may be weaker in isolation relative to "severe addiction"). Examples of n-gram categories and representative n-grams include:

Symptoms—Anxiety, withdrawal, severe, delusions, ADHD, weight, insomnia, drowsiness, suicidal, appetite, dizziness, nausea, episodes, attacks, sleep, seizures, addictive, weaned, swings, dysfunction, blurred, irritability, headache, fatigue, imbalance, nervousness, psychosis, drowsy;

Disclosure—Fun, play, helped, god, answer, wants, leave, beautiful, suffer, sorry, tolerance, agree, hate, helpful, haha, enjoy, social, talk, save, win, care, love, like, hold, cope, amazing, discuss;

Treatment—Medication, side effects, doctor, doses, effective, prescribed, therapy, inhibitor, stimulant, antidepressant, patients, neurotransmitters, prescriptions, psychotherapy, diagnosis, clinical, pills, chemical, counteract, toxicity, hospitalization, sedative, 150 milligram (mg), 40 mg, drugs;

Relationships/Life—Home, woman, man, she, him, girl, boy, game, friends, sexual, someone, movie, favorite, jesus, house, music, religion, her, songs, party, bible, relationship, hell, young, style, church, lord, father, season, heaven, dating;

Depression-Indicative—Loser, depressed, depression, depressing, lonely, sad, alone, weak, useless, life, imbalance, blame, problems, unsuccessful, suicidal, torture, safe, escape, worry, intimidate, uncomfortable, therapy, medication, pressure, conversation hurts, myself, worth, break, nobody, mine, painful, hate, suck; and Standard—Work, weekend, lol, say, friends, brilliant, follow, tips, love, amazing, hello, now, bored, awesome, beautiful, romantic, perfect, excited, smile, meet, tonight, life, movie, football, favorite, sleepy, great, night, team, good, anyone, you, your, tomorrow, money.

The analytics module 214 can perform one or more analytic processes using the contextual data 220. In some embodiments, the analytics module 214 performs an analytic processing using a segment of the contextual data 220 corresponding to a certain digital activity, a certain time interval, etc. Such action may be performed selectively. For instance, the analytics module 214 may only perform the analytic process(es) responsive to the valence estimation module 212 discovering that a digital activity does not match any entries in the personalized valence index. Examples of analytic processes include prioritizing recommendations for improving the health state of the subject, examining upward/downward trends in the health state as indicated by valence measures of digital activities performed over time, filtering certain data values from the contextual data 220 that are not to be examined by the index generation module 210 or the valence estimation module 212, etc.

Figure 3A:
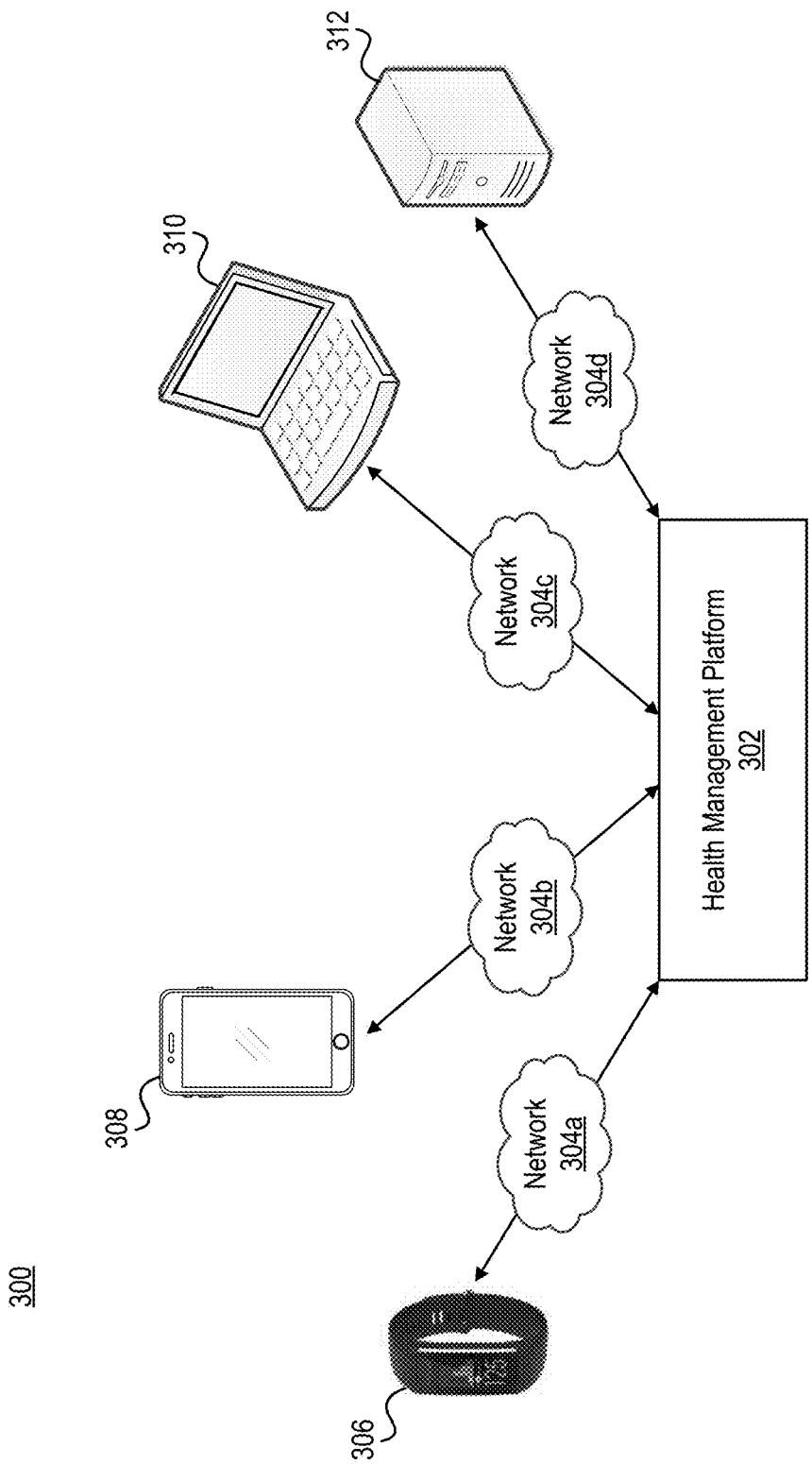
FIG. 3A depicts an example of a communication environment that includes a health management platform configured to receive contextual data from several different computing devices.

FIG. 3A depicts an example of a communication environment 300 that includes a health management platform 302 configured to receive contextual data from several different computing devices. Here, for example, the health management platform 302 receives contextual data from a fitness tracker 306, mobile phone 308, laptop computer 310, and network-accessible server system 312 (collectively referred to as the "networked devices").

The networked devices can be connected to the health management platform 302 via one or more computer networks 304a-d. The computer network(s) 304a-d can include PANs, LANs, WANs, MANs, cellular networks, the Internet, etc. Additionally or alternatively, the networked devices may communicate with one another over a short-range communication protocol, such as Bluetooth® or Near Field Communication (NFC). For example, the health management platform 302 may reside on the mobile phone 308 (e.g., in the form of a mobile application). In such embodiments, contextual data received from the mobile phone 308 need not traverse any computer networks. However, the mobile phone 308 may be communicatively coupled to the fitness tracker 306 via a Bluetooth® communication channel, the laptop computer 310 via a Wi-Fi communication channel, the network-accessible server system 312 via a cellular communication channel, etc.

Embodiments of the communication environment 300 may include some or all of the networked devices. For example, some embodiments of the communication environment 300 include a health management platform 302 that receives contextual data from the network-accessible server system 312 and the mobile phone 308 on which the health management platform 302 resides. As another example, some embodiments of the communication environment 300 include a health management platform 302 that only receives contextual data from the mobile phone 308 on which the health management platform 302 resides.

The networked devices may provide different types of contextual metadata. For example, the fitness tracker 308 may generate contextual data that specifies physical activities performed by the subject (e.g., swimming, running, or weightlifting) or provides a general indicator of activity level (e.g., in the form of a step count). As another example, the mobile phone 308 may generate contextual data specifying geographical locations traversed by the subject, social activities performed by the subject, etc.

Figure 3B:
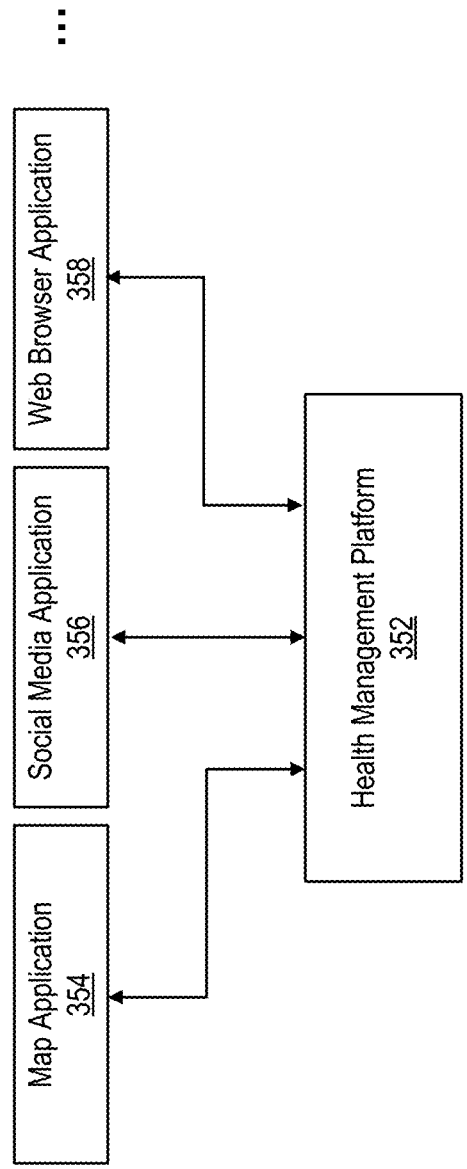
FIG. 3B depicts another example of a communication environment that includes a health management platform configured to receive contextual data from several different mobile applications.

FIG. 3B depicts another example of a communication environment 350 that includes a health management platform 352 configured to receive contextual data from several different mobile applications. Here, for example, the health management platform 352 receives contextual data from a map application 354, social media application 356, and web browser application 358. Those skilled in the art will recognize that these applications have been selected for the purpose of illustration only. Other applications (e.g., calendar applications, calling applications, messaging applications, music applications, video applications, etc.) may also be communicatively coupled to the health management platform 352. For example, a calendar application may generate contextual data specifying which scheduled appoints were attended, skipped, rescheduled, etc. The health management platform 352 may communicate with these applications through the use of APIs, bulk data interfaces, etc.

The health management platform 352 can identify occurrences of digital activities by examining the contextual data generated by these applications. Moreover, the health management platform 352 can virtually represent each digital activity based on corresponding contextual data. These virtual representations can be used to determine whether the corresponding digital activities are indicative of positive or negative valence.

For example, each time a subject uses the map application 354 to facilitate a movement activity, the map application 354 can generate contextual data that includes a record of movement activities involving the subject. Each movement activity can represent a digital activity, and the target of the digital activity may be a geographical location, such as the origination point and/or the destination point.

As another example, each time a subject uses the social media application 356 to facilitate a social activity, the social media application 356 can generate contextual data that includes a record of social activities involving the subject. Each social activity can represent a digital activity, and the target of the digital activity may be a social media identifier, such as a username, phone number, or email address.

As another example, each time a subject uses the web browser application 358 to facilitate an internet activity, the web browser application 358 can generate contextual data that includes a record of internet activities involving the subject. Each internet activity represents a digital activity, and the target of the digital activity may be the term(s) included in a search query, the Uniform Resource Locator (URL) of a visited website, etc.

Figure 4:
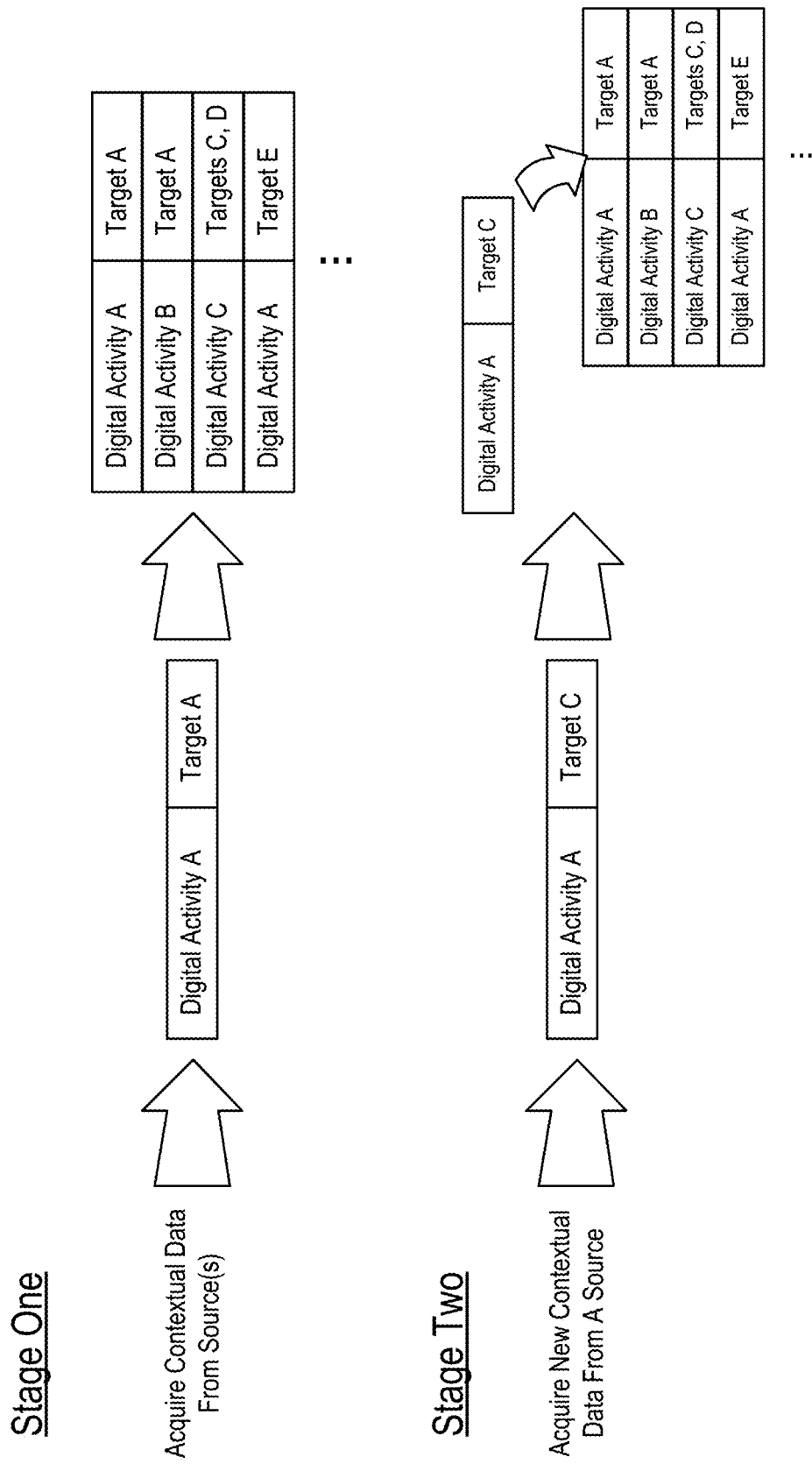
FIG. 4 includes a generalized illustration of a process for estimating the health state of a subject based on the digital activities performed by the subject.

FIG. 4 includes a generalized illustration of a process for estimating the health state of a subject based on the digital activities performed by the subject. During a first stage, a health management platform can acquire contextual data from one or more sources. Generally, the contextual data is known to be associated with the subject. For example, some contextual data may be generated by computing device(s) operated by the subject, while other contextual data may be generated by computer program(s) operated by the subject. For example, a mobile application executing on a mobile device may dynamically link contextual data generated by the mobile application with a credential or identifier used by the subject to access the mobile application.

The health management platform can examine the contextual data to identify occurrences of digital activities performed by the subject, and then identify the target(s) of each digital activity. Moreover, the health management platform can, for each identified digital activity, populate a database entry with the digital activity and the target(s). Thus, the health management platform can create electronic records of digital activities performed by the subject.

Database entries may share fields in common. Here, for example, the subject has completed a digital activity (i.e., Digital Activity A) twice, but each occurrence involved a different target (i.e., Targets A and E). The subject also completed two different digital activities (i.e., Digital Activities A and B) that involved the same target (i.e., Target A). Rather than include multiple database entries having the same fields, the health management platform may instead assign a weight to each database entry based on its frequency. Database entries appearing at higher frequencies are typically assigned larger weights. Such action enables the health management platform to distinguish between a database entry corresponding to a daily digital activity (e.g., a phone call to a family member) and a database entry corresponding to a weekly or monthly digital activity (e.g., a visit to a healthcare facility). The health management platform may more closely monitor for variations in high frequency digital activities than low frequency digital activities.

The health management platform can compile these database entries into a personalized valence index. Because the personalized valence index includes electronic records of digital activities typically performed by the subject, the personalized valence index can be interpreted as a digital characterization of the subject's typical health state. Said another way, the personalized valence index can provide a model of digital activities typically performed by the subject.

During a second stage, the health management platform can acquire new contextual data from a source. In some embodiments the source is one of the source(s) from which contextual data is acquired to construct the personalized valence index, while in other embodiments the source is distinct from these source(s).

The health management platform can examine the new contextual data to identify an occurrence of a recently completed digital activity performed by the subject, and then identify the target(s) of the recently completed digital activity. Here, for example, the health management platform has determined the subject performed Digital Activity A involving Target C. In some embodiments, the health management platform populates a new database entry with the digital activity and the target(s).

The health management platform can then estimate the valence of the recently completed digital activity. More specifically, the health management platform can monitor changes in the health state of the subject based on whether the recently completed digital activity is indicative of positive or negative valence. Valence concerns the intrinsic attractiveness ("goodness") or averseness ("badness") of a digital activity. Thus, a valence measure produced by the health management platform can characterize the specific emotional state(s) provoked by a corresponding digital activity. For example, anger and fear have negative valence measures, while joy and excitement have positive valence measures.

As noted above, the health management platform can estimate the valence of the recently completed digital activity by applying the personalized valence index to the newly populated database entry. Such a process may cause the health management platform to determine whether the digital activity and/or the target(s) included in the newly populated database entry match any existing database entries in the personalized valence index. Several different conclusions may be drawn based on whether a matching database entry is discovered.

If a matching database entry is found in the personalized valence index, then the health management platform may determine that the recently completed digital activity conforms with past digital activities performed by the subject. The health management platform often identifies matching database entries as having positive valence. Said another way, if a matching database entry is discovered, then the health management platform typically will not flag the recently completed digital action as possibly being indicative of a change in health state.

However, if a matching database entry is not found in the personalized valence index, then the health management platform may determine that the recently completed digital activity does not conform with any past digital activities involving the subject. While non-matching database entries do not necessarily have negative valence, they do represent digital activities the subject has not completed before. Accordingly, in such scenarios, the health management platform may flag the recently completed digital action as possibly being indicative of a change in health state.

For example, the health management platform may initially learn the valences associated with different digital activities (e.g., interactions with different individuals) based on self-reporting. In some embodiments, the health management platform may modify these valences based on prior values associated with the general population to speed up the learning process. For example, the health management platform may examine how a particular digital activity has affected/influenced other subjects. These other subjects may share a characteristic in common with the subject under review, such as age, sex, disease classification, etc. Digital activities that occur before a negative valence report (also referred to as a "low mood report") may have their weights reduced, while digital activities that occur before a positive valence report (also referred to as a "good mood report") may have their weights increased. Ongoing learning models can be used to capture valences that may vary/flip over time. Once a personalized valence model has been trained and is reliable, the overall valence measures produced by the personalized valence model may supplement or supplant the need for self-reporting. For example, if a subject reliably reports being in a better mood after going for a run and a worse mood after watching the news for an hour, then detecting either of these behaviors will bias the expected mood of the subject.

In some embodiments, the health management platform determines the valence measure of the recently completed digital activity by, for example, measuring a similarity between the recently completed digital activity and all entries in the personalized valence index. Different techniques can be employed to measure the similarity, including cosine similarity and clustering techniques such as K-means clustering. By implementing at least one of these techniques, the health management platform can measure the similarity between a measured matrix (e.g., of the recently pertained digital activity and corresponding target) and a baseline matrix. The baseline matrix could represent, for example, the personalized valence index. In some embodiments the baseline matrix is related to a category of digital activities (e.g., all activities involving news websites), while in other embodiments the baseline matrix is related to a specific source of digital activities (e.g., all activities involving a particular news website).

The health management platform can monitor several different metrics in order to discover the appropriate time to notify the subject or some other person that additional action(s) may be necessary. For example, the health management platform may monitor the valence measures of digital activities in real time to detect any valence measures that exceed a lower threshold (i.e., a certain negative valence). A digital activity may have negative valence due to its dissimilarity from all other digital activities performed by the subject, due to its natural valence, or any combination thereof. As another example, the health management platform may monitor the valence measures of digital activities in real time to detect a certain number of consecutive negative valence measures. Consecutive negative valence measures may be flagged for further review. Similarly, the health management platform may monitor the overall valence trend (e.g., whether valence values are trending upward or downward).

Generally, correlation between digital activities, targets, valence measures, and a health condition is initially discovered by examining a cohort of subjects. For example, a health management platform may determine that performance of, or involvement in, a certain digital activity is predictive of depression onset by observing those subjects in a cohort that have been diagnosed with depression. However, as noted above, a valence index representing a typical health state can be highly personalized based on the characteristics of a subject. For example, even if the health management platform determines that long periods of non-contact with friends and family is often indicative of increased depression, the health management platform may not categorize a subject as being at risk of depression unless that activity has been shown to be indicative of increased depression for that individual. This allows the health management platform to account for variations in how different subjects respond to different digital activities. For example, interactions with family members may be generate stress for some subjects and relieve stress for other subjects. The health management platform may examine both the variation in digital activities performed by the subject (e.g., whether a certain digital activity is being performed more or less frequently) and the simple performance of digital activities by the subject (e.g., whether a certain digital activity is being performed at all).

FIG. 5 depicts a flow diagram of a process 500 for generating a personalized valence index for a subject. A health management platform can, using the personalized valence index, examine contextual data associated with digital activities performed by a subject to determine whether the targets of those digital activities are indicative of positive or negative valence.

Initially, a health management platform acquires contextual data associated with a subject (step 501). In some embodiments the contextual data is acquired from a single source, while in other embodiments the contextual data is acquired from multiple sources. Examples of sources include the computing device on which the health management platform resides, a computer program executing on the computing device, another computing device, a computer program executing on the other computing device, etc. Thus, a health management platform embodied as a mobile application executing on a mobile phone may acquire contextual data from other mobile applications executing on the mobile phone in addition to, or instead of, one or more network-accessible databases.

In some embodiments, the contextual data includes a subject identifier. For example, the contextual data may include (or be accompanied by) metadata specifying credentials associated with the subject, a unique identifier generated by the health management platform or the source of the contextual data, the subject's name, etc. In such embodiments, a profile (also referred to as a "subject profile") maintained by the health management platform can be associated with the subject identifier. Thus, when the health management platform receives contextual data that includes the subject identifier, the health management platform can identify the appropriate subject profile to be configured.

The health management platform can then parse the contextual data to detect each digital activity represented by the contextual data (step 502). Moreover, the health management platform can identify the target(s) of each digital activity (step 503). Such action enables the health management platform to virtually represent each digital activity by digitally associating the digital action with the target(s). Generally, a virtual representation of a digital activity will specify the nature of the digital activity itself, as well as the target(s) of the digital activity. For example, a virtual representation of a communication activity may specify whether the communication activity was completed via a calling application, a messaging application, or an email application, and who the recipient(s) of the call, message, email, etc., are. As another example, a virtual representation of a movement activity may specify whether the movement activity was completed via walking, driving, or riding public transit, and the origination and/or destination points.

Thereafter, the health management platform can populate a database entry for each digital activity that associates the digital activity and its corresponding target(s) (step 504). The health management platform may also compile these database entries into a personalized valence index (step 505). The personalized valence index digitally characterizes the health state of the subject. Thus, the personalized valence index can be viewed as a model of digital activities typically performed by the subject (and the targets of those digital activities) that can be used to detect deviations in behavior.

Deviations in behavior may be indicative of changes in the health state. For example, upon discovering the subject has begun to submit different types of search queries or visit different types of websites, the health management platform may notify a health coach. As another example, upon discovering the subject has ceased calling a certain family member or friend, the health management platform may notify a health coach. Thus, the health management platform can monitor subject behavior to detect new behaviors that are not reflected in the personalized valence index, as well as detect the absence of past behaviors that are reflected in the personalized valence index.

In some embodiments, the health management platform is configured to update the personalized valence index responsive to detecting new digital activities or new targets in newly acquired contextual data (step 506). The personalized valence index may evolve over time based on subtle changes in behavior patterns. For example, the health management platform may be tuned to train the personalized valence index responsive to discovering minor behavioral changes and notify a health coach responsive to discovering major behavioral changes. The health management platform may determine that a behavioral change is minor if a limited number of digital activities or targets has changed but subject conduct has otherwise remained consistent.

FIG. 6 depicts a flow diagram of a process 600 for discovering changes in the health state of a subject through the application of a valence index. Steps 601-603 of FIG. 6 are substantially similar to steps 501-503 of FIG. 5.

After virtually representing the digital activity, a health management platform can access a valence index known to correspond to a certain health state (step 604). In some embodiments, the valence index is a personalized valence index created based on digital activities performed by the subject. In other embodiments, the valence index is a population-level valence index created based on digital activities performed by other subjects. As noted above, the valence index may correspond to a certain health state. For example, if the valence index is a personalized valence index, then the certain health state may be the normal health state of the subject. That is, the personalized valence index may be a model of digital activities typically performed by the subject. As another example, if the valence index is a population-level valence index, then the certain health state may be a physical, mental, or emotional condition. In such embodiments, the health management platform may have access to different population-level valence indices corresponding to depression, schizophrenia, diabetes, Crohn's disease, etc.

The health management platform can estimate the health state of the subject by comparing the digital activity or the target(s) to entries included in the valence index (step 605). Such action can be performed instead of, or in addition to, calculating the natural valence of the digital activity of the target(s) (e.g., based on a paralinguistic feature, non-linguistic feature, or linguistic feature). In some embodiments, the health management platform calculates a valence measure for the digital activity by determining whether the digital activity and/or the target(s) match any entries included in the valence index. Generally, the health management platform will determine that a "match" was found if a substantially similar digital activity or a substantially similar target is discovered.

The degree of matching can vary based on the similarity to the entries included in the valence index. For example, if the health management platform discovers a substantially similar digital activity, then the health management platform may determine that performance of the digital activity is not likely to be indicative of a change in the health state. Similarly, if the health management platform discovers a substantially similar target, then the health management platform may determine that performance of the digital activity is not likely to be indicative of a change in the health state. However, if the health management platform discovers a substantially similar digital activity and a substantially similar target, then the health management platform may determine that performance of the digital activity is even less likely to be indicative of a change in the health state.

The valence index can be leveraged by the health management platform in several other ways as well. For example, the health management platform may examine trends of the valence index over a specific time interval. Said another way, the health management platform may look at time series trends of the valence index. As another example, the health management platform may model changes in the health state as a state machine that jumps between states depending on a digital activity condition and/or a valence condition.

FIG. 7 depicts a flow diagram of a process 700 for generating a population-level valence index. Initially, a health management platform can receive input specifying whether digital activities, targets, or any combination thereof are indicative of positive valence or negative valence (step 701). For example, some digital activities (e.g., communicating with a family member, participating in a recreational activity, or attending a scheduled event) may be classified as having positive valence. As another example, some targets (e.g., family members, websites, or locations) may be classified as having positive valence. In some embodiments, the health management platform requires that groupings comprised of a digital event and one or more targets be classified as having positive valence or negative valence. Each digital activity or target could be manually classified by an individual, automatically classified by the health management platform, or any combination thereof. The health management platform may automatically classify digital activities and/or targeted based on, for example, the presence of a paralinguistic feature, non-linguistic feature, or linguistic feature.

The health management platform can then populate a database entry for each digital activity (step 702). Each database entry may associate a digital activity with one or more corresponding targets and/or a valence classification. Thus, the health management platform can readily identify database entries corresponding to digital activities and/or targets having negative valence and digital activities and/or targets having positive valence.

Moreover, the health management platform can compile the database entries into a valence index (step 703). The valence index may be referred to as a "population-level valence index" because its database entries do not correspond to a single subject. Instead, the database entries may be associated with digital activities performed by multiple subjects. Some database entries may not be associated with any subjects (e.g., the digital activity and target(s) may be entirely fabricated by the individual or health management platform).

The health management platform may also associate the population-level valence index with a certain health state (step 704). For example, the population-level valence index may correspond to depression, schizophrenia, diabetes, Crohn's disease, etc. Such action typically requires the health management platform know the subjects responsible for performing the digital activities characterized by the database entries share a certain health characteristic (e.g., a disease classification, state, or progression rate).

Similarly, the health management platform could generate a secondary population-level valence index by analyzing the personalized valence models for multiple subjects within a cohort. For example, the health management platform could generate a secondary population-level valence index for depression by compiling the personalized valence models associated with subjects suffering from depression. In such embodiments, certain features of each personalized valence index may be filtered so that they are not included in the secondary population-level valence index. For example, the health management platform may filter outlier database entries from each personalized valence index. An example of an outlier database entry is one that corresponds to a digital activity or target not included in any other personalized valence index to be compiled into the secondary population-level valence index. Another example of an outlier database entry is one that appears in the personalized valence index with a very low frequency (e.g., one or twice over an extended period of time).

In some embodiments personalized valence indices are built using the population-level valence index as a model, while in other embodiments personalized valence indices are built completely independently of the population-level valence index.

Unless contrary to physical possibility, it is envisioned that the steps described above may be performed in various sequences and combinations. For example, the health management platform may be configured to simultaneously apply a personalized valence index to digital activities recently performed by a subject and train the personalized valence index to be less sensitive to minor variations in subject behaviors.

Other steps may also be included in some embodiments. For example, the health management platform may notify a subject whose health state is being monitored and/or a health coach responsible for monitoring the health state of the subject. Such action may be performed, for example, responsive to a determination that a digital activity or target does not match any entries within a personalized valence index (and thus is indicative of a behavior change). As another example, such action may be performed responsive to a determination that a specified number of digital activities (e.g., 3, 5, or 7) occurring within a certain period of time (e.g., 1, 3, 5, or 7 days) do not match any entries within a personalized valence index (and thus are indicative of a significant behavior change).

More specifically, the health management platform may generate a count of new entries created for a personalized valence index over a certain time interval (e.g., a day, week, or month) and compare the count of new entries to a threshold. If the count of new entries exceeds the threshold, the health management platform may cause display of a notification that specifies the subject is likely to have experienced a change in the health state. The notification may be shown to the subject or a health coach responsible for monitoring the health state of the subject. Thus, the health management platform may monitor the personalized valence index to detect changes in health state.

As another example, the health management platform may identify a health state based on changes in the valence measure(s) associated with a subject. Said another way, while valence normally corresponds to health state (and changes in valence correspond to changes in health state), changes in valence could also be indicative of the health state. For instance, the health management platform may render bipolar diagnoses based on the speed of changes in valence measures (i.e., rather than any particular valence measure). Thus, the health management platform could identify a change in valence by comparing at least one recent valence measure (e.g., those within the first week of February) to at least one past valence measure (e.g., those within the first week of January), identify a time interval corresponding to the at least one recent valence measure and the at least one past valence measure (e.g., a month), and determine, based on the valence change and the time interval, a rate at which valence is changing.

Processing System

Figure 8:
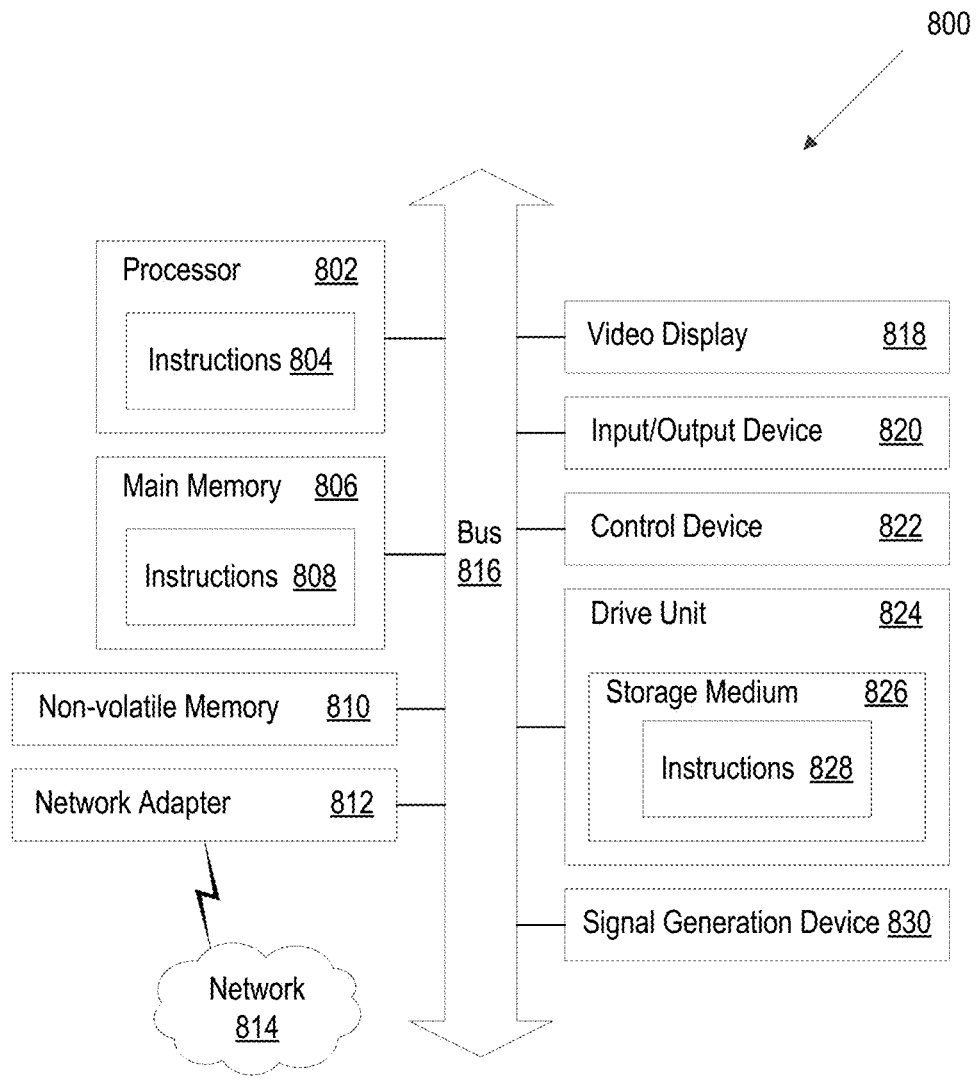
FIG. 8 is a block diagram illustrating an example of a processing system in which at least some operations described herein can be implemented.

FIG. 8 is a block diagram illustrating an example of a processing system 800 in which at least some operations described herein can be implemented. For example, some components of the processing system 800 may be hosted on a computing device that includes a health management platform (e.g., health management platform 102 of FIG. 1).

The processing system 800 may include one or more central processing units ("processors") 802, main memory 806, non-volatile memory 810, network adapter 812 (e.g., network interface), video display 818, input/output devices 820, control device 822 (e.g., keyboard and pointing devices), drive unit 824 including a storage medium 826, and signal generation device 830 that are communicatively connected to a bus 816. The bus 816 is illustrated as an abstraction that represents one or more physical buses and/or point-to-point connections that are connected by appropriate bridges, adapters, or controllers. The bus 816, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 800 may share a similar computer processor architecture as that of a desktop computer, tablet computer, personal digital assistant (PDA), mobile phone, game console, music player, wearable electronic device (e.g., a watch or fitness tracker), network-connected ("smart") device (e.g., a television or home assistant device), virtual/augmented reality systems (e.g., a head-mounted display), or another electronic device capable of executing a set of instructions (sequential or otherwise) that specify action(s) to be taken by the processing system 800.

While the main memory 806, non-volatile memory 810, and storage medium 826 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 828. The term "machine-readable medium" and "storage medium" shall also be taken to include any medium that is capable of storing, encoding, or carrying a set of instructions for execution by the processing system 800.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 804, 808, 828) set at various times in various memory and storage devices in a computing device. When read and executed by the one or more processors 802, the instruction(s) cause the processing system 800 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 810, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 812 enables the processing system 800 to mediate data in a network 814 with an entity that is external to the processing system 800 through any communication protocol supported by the processing system 800 and the external entity. The network adapter 812 can include a network adaptor card, a wireless network interface card, a router, an access point, a wireless router, a switch, a multi-layer switch, a protocol converter, a gateway, a bridge, bridge router, a hub, a digital media receiver, and/or a repeater.

The network adapter 812 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

REMARKS

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
   acquiring, by a processor, data pertaining to an activity performed by a first individual using a social media application executing on a computing device;
   analyzing, by the processor, the data to identify a social network identifier that is representative of a second individual involved in the activity;
   generating, by the processor, an electronic record of the activity that programmatically links the social network identifier with the activity performed by the first individual;
   calculating, by the processor, a valence measure to associate with the electronic record based on (i) the social network identifier and (ii) textual analysis of the activity;
   comparing, by the processor, the electronic record to entries of a personalized valence index associated with the first individual;
   configuring, by the processor, a profile associated with the first individual to include (i) an association between the valence measure and the electronic record of the activity and (ii) an indication whether a matching entry was found in the personalized valence index for the electronic record;
   establishing, by the processor, there has been a change in a health state of the individual based on a count of new entries generated in the personalized valence index over a preceding interval of time exceeding a threshold.

2. The method of claim 1, wherein the valence measure is based on paralinguistic analysis of the activity.

3. The method of claim 1, wherein the valence measure is based on non-linguistic analysis of the activity.

4. The method of claim 1, wherein the valence measure is based on linguistic analysis of the activity.

5. The method of claim 1, further comprising:
estimating, by the processor, the health state of the first individual by applying a personalized valence model to the profile.

6. The method of claim 5, wherein the personalized valence model is configured to produce an output indicative of the health state based on an analysis of valence measures associated with electronic records corresponding to another preceding interval of time.

7. The method of claim 1, wherein the valence measure characterizes how the first individual feels emotionally about the second individual, as inferred from the analysis of the activity.

8. The method of claim 1, further comprising:
establishing, by the processor, communication with a social media platform responsible for managing the social media application via an application programming interface (API);
wherein the data is acquired by the processor via the API.

9. The method of claim 1, wherein the processor is communicatively connected to the computing device across a network.

10. A non-transitory computer-readable medium with instructions stored thereon that, when executed by a processor, cause the processor to perform operations comprising:
acquiring contextual data pertaining to a digital activity performed by an individual;
parsing the contextual data to identify a target that is representative of an object of interest involved in the digital activity;
generating an electronic record of the digital activity by associating the digital activity and the target;
calculating, based on the target, a valence measure to associate with the electronic record by—
accessing a personalized valence index that includes entries representing past digital activities performed by the individual, and
comparing the electronic record to the personalized valence index;
configuring a profile to include an association between the valence measure and the electronic record; and
monitoring the personalized valence index to infer changes in a health state of the individual by—
generating a count of new entries in the personalized valence index that were created over a preceding interval of time,
comparing the count of new entries to a threshold, and
inferring that the health state of the individual has changed responsive to determining that the count of new entries exceeds the threshold.

11. The non-transitory computer-readable medium of claim 10, wherein the operations further comprise:
indicating in the profile whether a matching entry was found in the personalized valence index for the electronic record.

12. The non-transitory computer-readable medium of claim 10, wherein said calculating and said configuring are continually performed as contextual data pertaining to digital activities performed by the individual is received.

13. The non-transitory computer-readable medium of claim 12, wherein the operations further comprise:
monitoring valence measures included in the profile in such a manner that a trend in the valence measures can be identified in real time.

14. The non-transitory computer-readable medium of claim 10, wherein the operations further comprise:
determining that the electronic record does not match any entries in the personalized valence index; and
updating the personalized valence index by adding a new entry corresponding to the electronic record.

15. A method comprising:
acquiring, by a health management platform, contextual data pertaining to a digital activity performed by an individual;
analyzing, by the health management platform, the contextual data to identify a target that is representative of an object of interest involved in the digital activity;
generating, by the health management platform, an electronic record of the digital activity by associating the digital activity and the target;
calculating, by the health management platform, a valence measure to associate with the electronic record by—
comparing the electronic record to a personalized valence index that includes entries representing past digital activities performed by the individual, and
producing, based on an outcome of said comparing, the valence measure that is indicative of an emotional feeling of the individual with respect to the object of interest;
configuring, by the health management platform, a profile associated with the individual to include (i) an association between the valence measure and the electronic record of the digital activity and (ii) an indication whether a matching entry was found in the personalized valence index for the electronic record; and
monitoring, by the health management platform, the personalized valence index to detect changes in a health state of the individual by—
generating a count of new entries created for the personalized valence index over a preceding interval of time, and
inferring that the health state has changed responsive to determining that the count of new entries exceeds a threshold.

16. The method of claim 15, further comprising:
determining, by the health management platform, that the electronic record does not match any entries in the personalized valence index; and
updating, by the health management platform, the personalized valence index to include a new entry corresponding to the electronic record.

17. The method of claim 15, further comprising:
generating, by the health management platform, a notification that specifies the individual is likely to have experienced a change in health responsive to said inferring.

18. The method of claim 15, further comprising:
determining, by the health management platform, that the contextual data is associated with the individual based on the individual having previously logged into a source from which the contextual data is acquired.

19. The method of claim 15, further comprising:
identifying, by the health management platform, a first valence measure in the profile that is associated with a first point in time;

identifying, by the health management platform, a second valence measure in the profile that is associated with a second point of time following the first point in time; and determining, by the health management platform, a rate at which valence is changing over time by comparing the first and second valence measures, wherein the rate is indicative of a health trend of the individual.

20. The method of claim 15, wherein the object of interest is a person, an item, or a location involved in the digital activity.

\* \* \* \* \*